United States Patent
Douglas

(10) Patent No.: US 7,285,198 B2
(45) Date of Patent: Oct. 23, 2007

(54) STRIP ELECTRODE WITH CONDUCTIVE NANO TUBE PRINTING

(75) Inventor: Joel S. Douglas, Groton, CT (US)

(73) Assignee: MysticMD, Inc., Groton, CT (US)

( * ) Notice: Subject to any disclaimer, the term of this patent is extended or adjusted under 35 U.S.C. 154(b) by 303 days.

(21) Appl. No.: 11/063,504

(22) Filed: Feb. 23, 2005

(65) Prior Publication Data

US 2005/0186333 A1 Aug. 25, 2005

Related U.S. Application Data

(60) Provisional application No. 60/546,762, filed on Feb. 23, 2004.

(51) Int. Cl.
*G01N 27/327* (2006.01)
*G01N 27/30* (2006.01)

(52) U.S. Cl. .................. 204/403.14; 204/400

(58) Field of Classification Search ........... 204/400, 204/403.01–403.15; 205/775, 777.5, 778, 205/792

See application file for complete search history.

(56) References Cited

U.S. PATENT DOCUMENTS

| | | | |
|---|---|---|---|
| 4,224,125 A | 9/1980 | Nakamura et al. | |
| 4,225,410 A | 9/1980 | Pace | |
| 5,849,174 A | 12/1998 | Sanghera et al. | |
| 6,121,011 A | 9/2000 | Douglas et al. | |
| 6,245,215 B1 | 6/2001 | Douglas et al. | |
| 6,265,468 B1 | 7/2001 | Glatkowski et al. | |
| 6,309,535 B1 * | 10/2001 | Williams et al. | 205/777.5 |
| 6,493,208 B1 | 12/2002 | Piche et al. | |
| 6,582,573 B2 | 6/2003 | Douglas et al. | |
| 6,627,058 B1 * | 9/2003 | Chan | 204/403.15 |
| 2002/0035170 A1 | 3/2002 | Glatkowski et al. | |
| 2002/0143094 A1 | 10/2002 | Conroy et al. | |
| 2002/0180077 A1 | 12/2002 | Glatkowski et al. | |
| 2003/0008123 A1 | 1/2003 | Glatkowski et al. | |
| 2003/0122111 A1 | 7/2003 | Glatkowski et al. | |
| 2003/0164427 A1 | 9/2003 | Glatkowski et al. | |
| 2004/0099438 A1 | 5/2004 | Arthur et al. | |
| 2004/0262582 A1 * | 12/2004 | Kirkor et al. | 252/500 |

OTHER PUBLICATIONS

Wang et al. ("Carbon nanotube screen-printed electrochemical sensors," Analysts, 2004, 129, 1-2, published Dec. 9, 2003).*

* cited by examiner

*Primary Examiner*—Alex Noguerola
(74) *Attorney, Agent, or Firm*—Michaud-Duffy Group LLP

(57) ABSTRACT

An electrochemical test device for determining the presence or concentration of an analyte in an aqueous fluid sample comprises a substrate comprising a non-conductive material; a working electrode comprising a conductive film formed at least with carbon nanotubes, the working electrode having a first electrode area, a first lead and a first contact pad; a counter electrode comprising a conductive film formed at least with carbon nanotubes; a reagent capable of reacting with the analyte to produce a measurable change in potential which can be correlated to the presence or concentration of the analyte in the fluid sample, the reagent overlaying at least a portion of the first electrode area of the working electrode; and a reference electrode comprising a conductive coating formed at least with carbon nanotubes, the reference electrode having a third electrode area at least a portion of which is overlaid with a reference material.

44 Claims, 10 Drawing Sheets

STRIP ELECTRODE WITH CONDUCTIVE NANO TUBE PRINTING

REFERENCE TO RELATED APPLICATIONS

This invention claims priority to U.S. Provisional Application No. 60/546,762 entitled Strip electrode with conductive nano tube printing and methods, filed on Feb. 23, 2004 which is entirely and specifically incorporated by reference.

FIELD OF THE INVENTION

The invention relates to a carbon nanotube electrode with a modified surface, to a method of production of such an electrode, and to the use of such an electrode in bioelectrochemistry. The electrode can be connected by a conductive carbon, silver ink or conductive carbon nanotube trace that is capable of conducting the electrons from the bioelectrochemistry reaction to a meter that reads the bioelectrochemistry result.

BACKGROUND OF THE INVENTION

Various electrochemical sensors are known which employ enzymes to sense the presence of a compound that serves as an enzyme substrate. As just one example, Nakamura U.S. Pat. No. 4,224,125 discloses an enzyme electrode system in which an enzyme, such as glucose oxidase, is used to sense glucose. A redox compound is used to accept electrons from the enzyme. For example, Nakamura discloses press molding to the electrode a mixture of glucose oxidase cross-linked by gluteraldehyde and a fluorocarbon polymer powder together with a cation exchange resin containing potassium ferricyanide. Nakamura's electrode system consists of three electrodes: an enzyme electrode, a reference electrode, and a counter electrode.

In another example, U.S. Pat. No. 4,225,410 to Pace discloses a multi-layer enzyme sensor; for example a sensor that measures levels of lactate dehydrogenase. $NAD^+$ is generated at a fourth electrode, and the enzymatic reaction converts it to NADH which is sensed at the monitoring electrode by undisclosed means. A barrier/counter electrode and a reference electrode are used in conjunction with the monitoring electrode. However, the surface roughness of the electrodes and the difficulty in forming a well defined electrode causes the electro chemical reaction differences between strips. A means is needed to minimize this surface variation so that the strips manufactured give more repeatable results between strips and that the calibration effort is reduced.

Each of the above references is incorporated herein by reference in its entirety.

SUMMARY OF THE INVENTION

This invention relates to enzymatic sensor electrodes and their combination with reference electrodes to detect a compound in a liquid mixture. The electrodes are formed from a conductive layer made of carbon nanotubes and alloyed with other conductive and non conductive material such as carbon nanotubes, carbon nanotubes/antimony tin oxide, carbon nanotubes/platinum, or carbon nanotubes/silver or carbon nanotubes/silver-cloride and communicate electrically with conductive ink or conductive carbon nanotubes, carbon nanotubes/antimony tin oxide, carbon nanotubes/platinum, or carbon nanotubes/silver or carbon nanotubes/silver-cloride traces on the substrate.

The invention uses thin electrodes that have a very smooth surface morphology which permits the formation of surface texture less than 0.33 microns and nano size particles to produce well defined and smooth electrodes. The coating is formed from a conductive carbon nanotube coating which includes as part of the formulation carbon nanotubes, carbon nanotubes/antimony tin oxide, carbon nanotubes/platinum, or carbon nanotubes/silver or carbon nanotubes/silver-cloride. It can also be modified to use a platinum electrode by either integrating the platinum into the conductive carbon nanotube formulation or by applying it to the electrode surface. Either nano size platinum or aqueous platinum can be used for this purpose. These coatings when applied to a non conductive surface allow the production of an electrode that has very repeatable surface areas between different electrodes which improves consistency of biosensors made by the invention.

In addition, conductive coatings such as described in U.S. patent application Ser. No. 2002/0143094, Polymer Nanocomposites and Methods of Preparation, to Conroy et al.; U.S. patent application Ser. No. 2002/0035170, Electromagnetic Shielding Composite Comprising Nanotubes, to Glatkowski et al.; U.S. patent application Ser. No. 2002/0180077, Carbon Nanotube Fiber-Reinforced Composite Structures for EM and Lightning Strike Protection, to Glatkowski et al.; U.S. patent application Ser. No. 2003/0008123, Nanocomposite Dielectrics, to Glatkowski et al.; U.S. patent application Ser. No. 2003/0164427, ESD Coatings for Use with Spacecraft, to Glatkowski et al; and U.S. patent application Ser. No. 2003/0122111, Coatings Comprising Carbon Nanotubes and Methods for Forming Same, to Glatkowski et alall included herein by reference. The coatings made from the referenced patents and applications can be made from single wall or multi wall carbon nanotubes preferably sized to be less than 3.5 nm and greater than 0.1 nm in outer dimension size. Additionally conductive dispersions such as Acheson Electrodag 427 Antimony Tin Oxide (ATO) ink can be alloyed with either single wall or multi wall carbon nanotubes preferably sized to be greater than 3.5 nm and less than 10 nm in outer dimension size. The carbon nano tubes are mixed uniformly into the Acheson Electrodag 427 such that the percent by weight is between 0.5 to 10%. Preferably the carbon nano tubes are added such that they make up 3% by weight of the mixture. Additionally platinum nano particles can be added and mixed uniformly to the coating such that the percent by weight is between 0.5 to 10%. Preferably the nano size platinum particles are added such that they make up 4% by weight of the mixture. Each of the above references is incorporated herein by reference in its entirety. The resulting coating thicknesses are between about 0.5 nm to about 1000 microns Any of the aforementioned coatings result in improved electrode repeatability, total light transmittance of greater than 70% and reduced haze value less than 2.0%, and the film has a surface resistance in the range of less than about 50,000 ohms/square.

One aspect of the invention generally features a multi-electrode strip for releasable attachment to signal readout circuitry, forming a sensor system that detects a current representative of a compound in a liquid mixture. The strip comprises an elongated support (preferably flat) adapted for releasable attachment to the readout circuitry. A first conductorand a second conductor each extend along the support and comprise a means for connection to the circuitry. An active electrode, positioned to contact the liquid mixture and the first conductor, comprises a deposit of an enzyme capable of catalyzing a reaction involving the compound.

Electrons are transferred between the enzyme-catalyzed reaction and the first conductor to create the current. A reference electrode is positioned to contact the mixture and the second conductor.

The preferred embodiment of the strip includes the following features: a conductive carbon nanotube electrode formed by coating the substrate with a conductive carbon nanotube solution similar to that found in U.S. patent application Ser. No. 2003/0122111, to Glatkowski, or U.S. Pat. No. 6,265,466 to Glatkowski et al. and U.S. Pat. No. 6,493,208 to Piche et al. Each of the above referenced patents is incorporated herein by reference in its entirety.

In addition conductive coatings such as described in U.S. patent application Ser. No. 2002/0143094, Polymer Nanocomposites and Methods of Preparation, to Conroy et al., U.S. patent application Ser. No. 2002/0035170, Electromagnetic Shielding Composite Comprising Nanotubes, to Glatkowski et al., U.S. patent application Ser. No. 2002/0180077, Carbon Nanotube Fiber-Reinforced Composite Structures for EM and Lightning Strike Protection, to Glatkowski et al., U.S. patent application Ser. No. 2003/0008123, Nanocomposite Dielectrics, to Glatkowski et al., U.S. patent application Ser. No. 2003/0164427, ESD Coatings for Use with Spacecraft, to Glatkowski et al., and U.S. patent application Ser. No. 2003/0122111, Coatings Comprising Carbon Nanotubes and Methods for Forming Same, to Glatkowski et al., all included herein by reference. The coatings made from the referenced patents and applications can be made from single wall or multi wall carbon nanotubes preferably sized to be less than 3.5 nm and greater than 0.1 nm in outer dimension size. Additionally conductive dispersions such as Acheson Electrodag 427 Antimony Tin Oxide (ATO) ink can be alloyed with either single wall or multi wall carbon nanotubes preferably sized to be greater than 3.5 nm and less than 10 nm in size to achieve a coating that allows for improved surface which permits the formation of surface texture less than 0.33 microns and improved repeatability of the edges of the electrode shape. The carbon nano tubes are mixed uniformly into the Acheson Electrodag 427 such that the percent by weight is between 0.5 to 10%. Preferably the carbon nano tubes are added such that they make up 3% by weight of the mixture. Additionally platinum nano particles can be added and mixed uniformly to the coating such that the percent by weight is between 0.5 to 10%. Preferably the nano size platinum particles are added such that they make up 4% by weight of the mixture. Each of the above referenced patents is incorporated herein by reference in its entirety.

Additionally the electrodes are formed such that they provide well defined areas as well as having smooth surface morphology. The improved surface morphology is attained by the carbon nanotubes, carbon nanotubes/antimony tin oxide, carbon nanotubes/platinum, or carbon nanotubes/silver or carbon nanotubes/silver-cloride dispersion or coating. The small size permits the formation of surface texture less than 0.33 microns. These conductive coatings knit together to form a conductive trace and the overlaying of the polymer binder or dispersion within a polymer binder provides a porous layer that allows the passage of the electrons formed from the electrochemical reaction. The well defined electrode shapes can be accomplished by different methods. The first being inkjet printing where an inkjet printer applies the image of the electrode with an ink containing conductive carbon nanotube material. Then a binder polymer is applied leaving behind well defined electrodes with a smooth surface morphology. The polymer binder is not conductive therefore the electrodes laid down in the first step are the only conductive paths. The ink jetting can be accomplished by using precision components from the Lee Company of Westbrook, Conn., such as the VHS-S/P 10+ Nanoliter Dispensing Valves.

The polymeric material is selected from the group consisting of thermoplastics, thermosetting polymers, elastomers, conducting polymers and combinations thereof; or the polymeric material comprises a material selected from the group consisting of polyethylene, polypropylene, polyvinyl chloride, styrenic, polyurethane, polyimide, polycarbonate, polyethylene terephthalate, cellulose, gelatin, chitin, polypeptides, polysaccharides, polynucleotides and mixtures thereof, or ceramic hybrid polymers, Ethylene Glycol Monobuti Ether Acetate, phosphine oxides and chalcogenides. Alternatively a polymeric material wherein the conductive elements are dispersed substantially homogenously or in a gradient throughout the polymeric material can be used such as the Acheson Electrodag PF 427.

The second most preferred means of forming a well defined film electrode is to apply the conductive carbon nanotube layer uniformly to the substrate and then screen print the polymer binder to protect only the electrode regions. The unprotected carbon nanotube material is removed leaving only the finished electrodes.

The third most preferred means is to print the conductive carbon nanotube layer in the required pattern using a template or mask. Then the polymer binder is applied to the entire surface. The polymer binder is not conductive therefore the electrodes laid down in the first step are the only conductive paths.

The fourth most preferred means of forming a well-defined electrode is to apply the conductive carbon nanotube ink either in a two pass system or one pass system. In the one pass system the binder and nanotubes and other conductive components of the ink are in the same dip. In the two pass system the nanotubes are applied first by either printing, spraying coating, or dip coating and the polymer binder is applied second after the first pass is dried. U.S. Pat. No. 6,121,011 issued to Douglas et al., Methods for applying a reagent to an analytical test device describes various nozzle based and brush based coating means useful in applying the conductive carbon nanotube ink. However, one skilled in the art can reverse this order and achieve excellent results. The coating is then formed into electrodes by laser cutting or etching the electrodes.

The fifth most preferred means is to apply the one pass system where the binder and nanotubes are in the same dip and then using standard photoliograph, screen printing or ink jetting methods to form the electrodes. Photo definable electrode manufacturing is described in U.S. Pat. No. 6,245,215 issued to Douglas et al., Membrane based electrochemical test device and related methods and U.S. Pat. No. 6,582,573 issued to Douglas et al., Membrane based electrochemical test device, their disclosure is included by in there entirety by reference.

Once the electrodes have been suitably formed an electron mediator (most preferably a ferrocene or Imidozole Osmium mediator is applied to the active electrode. The osmium mediator allows the reaction to occur with a very low potential or voltage between the electrodes. It is included in the active electrode deposit to affect the electron transfer. The compound being detected is glucose, and the enzyme is glucose oxidase or glucose dehydrogenase. The active electrode and the reference electrode are carbon nanotube based coatings applied to the elongated support, e.g. the active electrode is formed by printing (e.g., screen printing, ink jetting, or other printing means) the conductive carbon nanotube mixture, the enzyme and the mediator, and the reference electrode is also formed by printing the conductive carbon nanotube mixture. The means for connecting to the readout circuit are formed from an ink comprising a conductive compound positioned toward one end of the elongated support, and the conductive carbon nanotube electrodes are positioned remote from that end.

The requirement for the use of a mediated chemistry can be eliminated by forming one or more of the electrodes with platinum nano particles or by adding or applying aqueous platinum to the electrode. This then forms a traditional platinum electro chemical sensor system.

In another aspect, the invention features screen printing the enzyme onto a substrate to form an enzymatic sensing electrode. The conductive carbon nanotube mixture is comprised of solutions formed from either carbon nanotubes, carbon nanotubes/antimony tin oxide, carbon nanotubes/platinum, or carbon nanotubes/silver or carbon nanotubes/silver-cloride used for printing the electrode and includes a second coat of a liquid polymer, or a suspension of conductive material such as carbon nanotubes, carbon nanotubes/antimony tin oxide, carbon nanotubes/platinum, or carbon nanotubes/silver or carbon nanotubes/silver-cloride suspended in a suitable polymer. The enzyme is applied as a second step and preferably, it also includes a mediator capable of transferring electrons between the enzymatic reaction and a conductor on the substrate when used with a non platinized sensor configuration. Also preferably, the substrate is a flexible, high-dielectric polymeric substance, such as polyvinyl chloride, polyester, or polycarbonate.

The invention enables a very small, inexpensively manufactured, disposable electrode strip that provides an accurate electronic readout of the target compound. In particular, the active electrode is sized to be covered by a small amount of body fluid produced from a drop of blood or interstitial fluid (ISF) generated from a needle-prick, laser cut, or microporation technique on the body, and the reference electrode is sized and spaced from the active electrode a distance such that the reference electrode is covered by the same small amount of body fluid. Additionally the very repeatable surface formed by the conductive mixtures or dispersions of carbon nanotubes, carbon nanotubes/antimony tin oxide, carbon nanotubes/platinum, or carbon nanotubes/silver or carbon nanotubes/silver-clorideand the well defined area formed by the deposition methods of the invention form a consistent surface morphology. The electrode formed by the invention results in a more consistent surface area thereby minimizing strip to strip variation in manufacturing due to the improved surface morphology and the improved electrode definition.

The use of the transparent conductive carbon nanotubes, carbon nanotubes/antimony tin oxide, carbon nanotubes/platinum, or carbon nanotubes/silver or carbon nanotubes/silver-cloride coatings also permits the manufacturer from having alternative brand test strips used in their meters. This allows inferior or poorly manufactured product to be detected and prevented from being used in the test device. The transparent nature of the conductor when used with an appropriately configured LED and detector system can prevent the utilization of non branded product being used in the test device.

The ability to form well formed boundaries and smooth surface morphology (the coatings of this invention permits the formation of surface texture less than 0.33 microns) permits the electrodes formed by the use of this invention to be more repeatable and therefore more consistent from electrode to electrode when manufacturing large numbers of electrodes. Electro chemical detection using enzymatic means is sensitive to the surface area of the electrode. Therefore variation in surface area results in different response from electrode to electrode. The consistent boundary and smooth surface morphology makes the electrode surface area more consistent between test strips manufactured from existing processes that use large particle carbon and conductive inks. The large size of the current carbon particles require that the screen mesh be large enough to allow the conductive particles to pass. The larger mesh further increases the surface area consistency between strips by the rough edges of the electrode. Both variables of rough surface and electrode rough edge profile make consistency between test strips difficult and therefore requires the manufacturer to spend considerable time and effort to sort and calibrate the electrodes.

The small size of the nano particles and the high conductivity of nano size particles allow the electrodes made with this invention to be more consistent and repeatable. Nano tubes and dispersions made from nano tubes that are at least less than 20 nm in diameter form a very consistent electrical conductive path. In addition the ability to form the electrode shapes in a highly repeatable and accurate form allows the electrodes to be positioned closer together than the current materials and processes allow. This has an added advantage of permitting the sample size used to be smaller because the sample must cover the electrodes for the system to work. An electrode set that is positioned closer together requires less sample size to get an electrochemical result. Furthermore this high electrical conductivity coupled with small size and improved surface morphology results in a bio sensor that is consistently better than current carbon and silver screen printed electrodes. The resulting film has a surface resistance in the range of less than about 50,000 ohms/square and total light transmittance of greater than 70% as well as reduced haze value less than 2.0%. The resulting coating thicknesses are between about 0.5 nm to about 1000 microns Other features and advantages of the invention will be apparent from the following description of the preferred embodiments.

DESCRIPTION OF THE INVENTION

Electrode Structure

Figure 1:
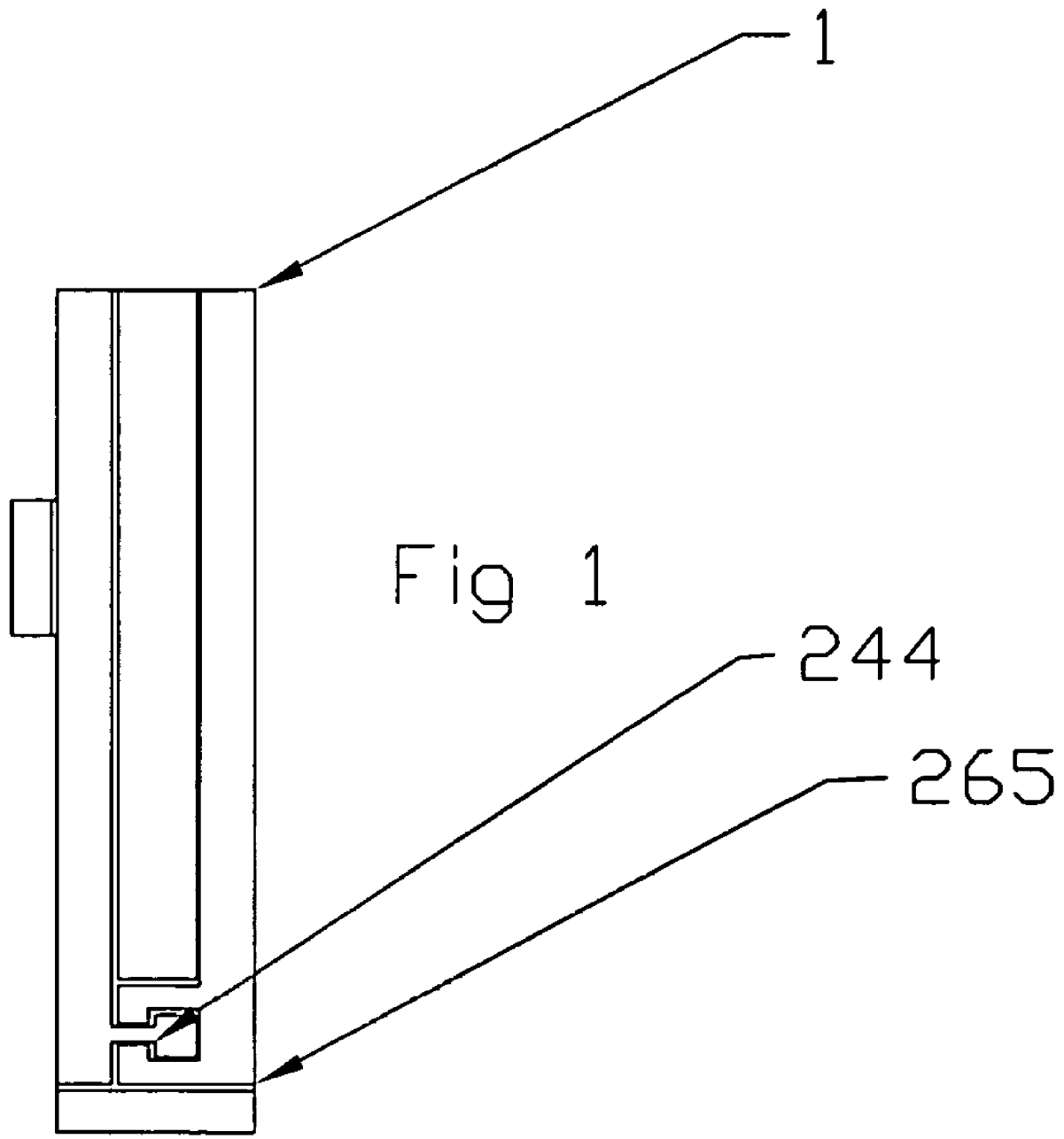
FIG. 1 is a front of a strip-supported electrode configuration.

In general, the strip electrode of the invention comprises a conductive electrode coated with a mixture of conductive carbon nanotubes or dispersion made from carbon nanotubes/antimony tin oxide, carbon nanotubes/platinum, or carbon nanotubes/silver or carbon nanotubes/silver-cloride, formed by coating the substrate with a conductive carbon nanotube solution similar to that found in conductive coatings such as described in U.S. patent application Ser. No. 2002/0143094, Polymer Nanocomposites and Methods of Preparation, to Conroy et al., U.S. patent application Ser. No. 2002/0035170, Electromagnetic Shielding Composite Comprising Nanotubes, to Glatkowski et al., U.S. patent application Ser. No. 2002/0180077, Carbon Nanotube Fiber-Reinforced Composite Structures for EM and Lightning Strike Protection, to Glatkowski et al., U.S. patent application Ser. No. 2003/0008123, Nanocomposite Dielectrics, to Glatkowski et al., U.S. patent application Ser. No. 2003/0164427, ESD Coatings for Use with Spacecraft, to Glatkowski et al., and U.S. patent application Ser. No. 2003/0122111, Coatings Comprising Carbon Nanotubes and Methods for Forming Same, to Glatkowski or made from coatings as described in U.S. Pat. No. 6,265,466 to Glatkowski et al. and U.S. Pat. No. 6,493,208 to Piche et al., all included herein by reference or made from dispersions of carbon nanotubes, carbon nanotubes/antimony tin oxide, carbon nanotubes/platinum, or carbon nanotubes/silver or carbon nanotubes/silver-cloride, and a catalytically active enzyme and an optional mediator compound. The resulting film has a surface resistance in the range of less than about 50,000 ohms/square, total light transmittance of greater than 70% as well as reduced haze value less than 2.0% prior to application of the catalytically active enzyme and the resulting coating thicknesses are between about 0.5 nm to about 1000 microns. When such a coated electrode is contacted with a substrate containing an analyte for which the enzyme exerts a catalytic effect, the mediator compound transfers a charge to the electrode and this can be used to give a readout signal, against a standard electrode, correlated with the concentration of the said analyte, even in the presence of other analytes since enzymes are typically highly selective in their catalytic action. U.S. Pat. No. 5,849,174 generally describes methods of coating a conductive electrode with enzyme and mediator; that application is hereby incorporated herein by reference. The mediator compounds described in U.S. Pat. No. 5,849,174 include polyviologens, fluoranil and chloranil. However, the preferred mediator compounds are metallocene compounds, and in particular the ferrocenes (biscyclopentadienyl iron and its derivatives) or Imidozole Osmium mediator. Osmium mediator allows the reaction to occur with a very low potential or voltage between the electrodes. Each of the above referenced patents is incorporated herein by reference in its entirety.

The particular enzyme employed may be selected from a range of enzymes including the following:

| Enzyme | Substrate |
| --- | --- |
| Pyruvate Oxidase | Pyruvate |
| L-Amino Acid Oxidase | L-Amino Acids |
| Aldehyde Oxidase | Aldehydes |
| Xanthine Oxidase | Xanthines |
| Glucose Oxidase | Glucose |
| Glycollate Oxidase | Glycollate |
| Sarcosine Oxidase | Sarcosine |
| Lactate Oxidase | Lactate |
| Glutathione Reductase | NAD(P)H |
| Lipoamide Dehydrogenase | NADH PQQ Enzymes |
| Glucose Dehydrogenase | Glucose |
| Methanol Dehydrogenase | Methanol and Other Alkanols |
| Methylamine Dehydrogenase | Methylamine Haem-Containing Enzymes |
| Lactate Dehydrogenase | Lactate(Yeast Cytochrome b2) |

-continued

| Enzyme | Substrate |
| --- | --- |
| Horse-Radish Peroxidase | Hydrogen Peroxide |
| Peroxidase | Hydrogen Peroxide |
| Galactose Oxidase | Galactose |

The strip electrode has the following design criteria. The electrodes on the strip should be as small as possible and the strip should preferably be disposable. The strip should be elongate for ready handling as an electrode for ready assembly to equipment on the one hand and contact with the sample on the other. It must be sensitively manipulable. It may carry, prior to assembly or in the assembled structure, the reference electrode as well as the 'sensitive' electrode, in spaced non-contiguous relationship.

The invention is particularly useful for selective detection, measurement or monitoring of a given dissolved analyte in a mixture of dissolved analytes.

The elongate support could be any shape, but conveniently it comprises a flat strip. A flat strip has been found to help achieve the smoothest surface morphology (this permits the formation of surface texture less than 0.33 microns) and the least variation in edge profile.

By way of example only, conductive carbon nanotube electrodes of the invention can be formed on the strip; Imidozole Osmium mediator can be deposited on the surface of the conductive carbon nanotube electrode by evaporation of a toluene solution; and enzyme can be bonded to the surface by the use of 1-cyclohexyl-3-(2-morpholinoethyl) carbodiimide metho-p-toluene sulphonate (referred to below as "carbodiimide").

The reference electrode can be any convenient reference electrode. We have found it useful to provide adjacent but not contiguous to the first electrode, a flat layer of silver and to convert the surface thereof to silver chloride so as to give an Ag/AgCl reference electrode. This can be accomplished by alloying the conductive carbon nanotube material with nano size AG/AGCL material or by applying a colloidal AG/AGCL mixture into or onto the conductive carbon nanotube electrode. This method can also be used to form a platinum electrode which is desirable in some instances because it eliminates the need for the mediator and it also increases the electrode's sensitivity to the oxidase reaction.

Typically, the electrical connections can be metal contacts which extend down, and preferably contact the strip electrodes, and make electrical contact each with its respective electrode.

The readout means is preferably a digital indicator suitably connected to a dedicated potentiostat which poises the electrode potential at e.g. +150 mV vs. Ag/AgCl for a glucose system. The current flowing is then proportional to glucose concentration.

In a particular version of this type of sensor that has only two electrodes but is consistent with three electrode embodiments, it comprises:

(a) a flat first electrode area of known area small enough to be completely coverable by the small amount of body fluid produced from lancing or laser hole, etc. The body fluid generated is applied to the active electrode which is treated with the appropriate reagent formulation to produce a consistent electro chemical result. When the active electrode known area is formed from the conductive carbon nanotube materials of the invention by one of the preferred methods then the surface morphology which is less than 0.33 microns and the repeatable boundary forms an excellent and repeatable first electrode.

(b) (b) a reference electrode area on the same surface separate from but sufficiently close to the sensitive electrode area that the said body fluid also reaches the reference electrode to establish electrical communication; and (c) (c) conductive elements extending separately along the same surface of, and thus insulated from the elongate support member, communicating one with each electrode for connection to a signal readout means attachable to one end of the member.

The ability to form well formed boundaries and smooth surface morphology permits the electrodes formed by the use of this invention to be more repeatable and therefore more consistent from electrode to electrode when manufacturing large numbers of electrodes. The small size of the conductive particles allows the surface morphology to be less than 0.33 microns. Electro chemical detection using enzymatic means is sensitive to the surface area of the electrode. Therefore variation in surface area results in a different response from electrode to electrode. The boundary and smooth surface morphology makes the electrode surface area more consistent between test strips manufactured from existing processes that use large particle carbon and conductive inks. The large size of the carbon particles require that the screen mesh be large enough to allow the conductive particles to pass. The larger mesh further increases the surface area consistency between strips by the rough edges of the electrode. Both variables of smooth surface and electrode rough edge profile make consistency between test strips difficult and therefore requires the manufacturer to spend considerable time and effort to sort and calibrate the electrodes. In addition the ability to form the electrode shapes in a highly repeatable and accurate form allows the electrodes to be positioned closer together than the current materials and processes allow. The repeatable and consistent formation of electrodes is an advantage because it permits the sample size used to be smaller because the sample must cover the electrodes for the system to work. An electrode set that is positioned closer together requires less sample size to get an electrochemical result. Furthermore the high electrical conductivity of these coatings coupled with small size and improved surface morphology results in a bio sensor that is consistently better than current carbon and silver screen printed electrodes.

As an example, the area of the first (i.e. sensitive or active) electrode is generally substantially square; although it may be rectangular or otherwise shaped, but in any case usually will correspond in area to a square of 5 mm edge length, or below e.g., from about 2 to about 4 mm.

For convenience, this document will refer hereinafter to body fluid -glucose-measuring equipment as being typical but not limitative of equipment with which the present invention is concerned.

An example reagent formulation suitable for use in the present invention is described below. This reagent may be used to determine the presence or concentration of glucose in an aqueous fluid sample. Preferably, this reagent formulation is used with an electrochemical sensor having an opposing electrode 3, working electrode 2 and reference electrode 5.

| Reagent Formulation | |
|---|---|
| Material | Amount/Concentration |
| 2-(N-morpholino)ethanesulfonic acid | 100 millimolar (mM) (MES buffer) |
| Triton X-100 | 0.08% wt/wt |
| Polyvinyl alcohol (PVA) mol. wt. 10K 88% hydrolized | 1.00% wt/wt |
| Imidazole osmium mediator, reduced, as defined in U.S. Pat. No. 5,437,999 | 6.2 mM |
| Glucose Oxidase | 6000 units/mL |

The above reagent formulation may be prepared using the following procedures:

(a) 1.952 grams of MES buffer is added to 85 mL of water. The mixture is stirred until the components dissolve. The pH of the solution is adjusted to 5.5 with NaOH. The volume of the solution is then brought to 100 mL of final buffer solution.

(b) 0.08 grams of Triton X-100 and 1 gram of PVA is added to a beaker capable of holding all the components (e.g., a 200 mL beaker). The buffer solution is added to bring the total solution weight to 100 grams. The mixture is heated to boiling and stirred to dissolve the PVA.

(c) 4.0 mg of the reduced osmium mediator is added to 1 mL of the solution from step (b) above. The mixture is stirred to dissolve the mediator.

(d) The mixture is left to cool to room temperature.

(e) 6000 units of glucose oxidase are added and the mixture is mixed until the enzyme is dissolved.

The above reagent formulation may be used to determine the presence or concentration of glucose in an aqueous fluid sample. As will be apparent to those skilled in the art, other reagent formulations may be employed to assay different analytes. Such reagent formulations are well known in the art. Typically, such reagent formulations are designed to react specifically with the desired analyte to form a measurable electrochemical signal.

Without being limited to theory, it is believed that in the example reagent formulation described above, glucose is anaerobically oxidized or reduced with the involvement of the enzyme and the redox mediator. Such a system is sometimes referred to as an amperometric biosensor. Amperometry refers to a current measurement at constant applied voltage on the working electrode. In such a system, the current flowing is limited by mass transport. Therefore, the current is proportional to the bulk glucose concentration. The analyte, enzyme and mediator participate in a reaction where the mediator is either reduced (receives at least one electron) or oxidized (donates at least one electron). The glucose reaction ends when glucose oxidase is oxidized and the mediator is reduced. The mediator is then oxidized at the surface of the working electrode by the applied potential difference. Changes in the system amperage result from changes in the ratio of oxidized/reduced form of the redox mediator. The amperage change directly correlates to the detection or measurement of glucose in the test sample. However, the carbon nanotube conductive coating works equally as well when used in a test strip based on coulometry measurements. Coulometry measures virtually all the analyte in a sample which enables the use of very small samples.

Various enzymes may be used in the reagent formulations employed in this invention. The particular enzyme employed will vary depending on the analyte to be detected or measured. Preferred enzymes include glucose oxidase, glucose dehydrogenase, cholesterol esterase and alcohol oxidase. The amount of enzyme employed will generally range from about 0.5 to about 3.0 million units of enzyme per liter of reagent formulation.

The reagent formulation will also typically contain a redox mediator. The redox mediator will generally be chosen to be compatible with the enzyme employed and combinations of redox mediators and enzymes are well known in the art. Suitable redox mediators include, by way of example, imidazole osmium mediator, potassium ferricyanide and ferrocene derivatives, such as 1,1.cent.-dimethyl ferrocene, or Imidozole Osmium. The amount of redox mediator employed in the reagent formulation will typically range from about 0.15 M to about 0.7 M. Additional mediators suitable for use in this invention include methylene blue, p-benzoquinone, thionine, 2,6-dichloroindophenol, gallocyanine, indophenol, polyviologen, osmium bis (2,2.cent.-bipyridine) dihydrochloride, and riboflavin-5.cent.-phosphate ester. Optionally, these mediators can be chemically bound or entrapped in a matrix, such as a polymer, using procedures well known in the art.

Examples of enzyme/mediator combinations suitable for use in this invention include, but are not limited to, the following:

| Analyte | Enzyme | Mediator |
| --- | --- | --- |
| glucose | glucose dehydrogenase | ferricyanide |
| glucose | glucose oxidase | tetracyanoquinodimethane |
| cholesterol | cholesterol esterase | ferricyanide |
| alcohol | alcohol oxidase | phenylenediamine |
| glucose | glucose oxidase | imidazole osmium mediator |

A preferred reagent chemistry uses imidazole osmium mediator as a mediator or 1,1' dimethyl ferrocene.

In addition to an enzyme and a redox mediator, the reagent layer on the electrode preferably further comprises a buffer, a stabilizer, a dispersant, a thickener or a surfactant. These materials are typically employed in amounts which optimize the reaction of the reagents with the analyte. The concentration ranges for these components referred to below are for the reagent formulation before it has dried on the electrode surface.

A buffer is preferably employed in the reagent formulation to provide a satisfactory pH for enzyme function. The buffer used must have a higher oxidation potential than the reduced form of the redox mediator. A preferred buffer for use in this invention is a phosphate buffer having a concentration ranging from about 0.1 M to about 0.5 M. Other suitable buffers include BES, BICINE, CAPS, EPPS, HEPES, MES, MOPS, PIPES, TAPS, TES and TRICINE buffers (collectively known as 'GOOD' buffers), citrate, TRIS buffer, and the like. The 'GOOD' and TRIS buffers are commercially available from Sigma-Aldrich, Inc. (St. Louis, Mo., U.S.A.).

A stabilizer may also be employed in the reagent formulation to stabilize the enzyme. When the enzyme used is glucose oxidase, a preferred stabilizer is potassium glutamate at a concentration ranging from about 0.01 to 4.0% weight. Other suitable stabilizers include succinate, aspartate, blue dextran and the like.

Additionally, dispersants may be used in the reagent formulation to enhance the dispersion of the redox mediator and to inhibit its recrystallisation. Suitable dispersants include microcrystalline cellulose, dextran, chitin and the like. Typically, the dispersant is used in the reagent formulation in an amount ranging from about 1.0 to about 4.5% weight. Preferred dispersants include, but are not limited to, AVICEL RC-591 (a microcrystalline cellulose available from FMC Corp.) and NATROSOL-250 M (a microcrystalline hydroxyethylcellulose available from Aqualon).

A thickener may also be employed in the reagent formulation to hold the reagent to the electrode surface. Suitable thickeners include water-soluble polymers, such as polyvinylpyrrolidone.

Additionally, a surfactant may be added to the reagent formulation to facilitate rapid and total wetting of the electrode surface. Preferably, the reagent formulation contains a nonionic surfactant in an amount ranging from about 0.01 to 0.3% by weight. A preferred surfactant is TRITON X-100, available from Sigma-Aldrich, Inc.

The working electrode can be made by different ways.

FIG. 1 shows a front view of a strip electrode where the strip 1 and electrodes 244 and 265 are formed from the same conductive material of this invention. The material formed from single-walled or multi walled nanotubes and may be formed from multiple layers or dispersions containing, carbon nanotubes, carbon nanotubes/antimony tin oxide, carbon nanotubes/platinum, or carbon nanotubes/silver or carbon nanotubes/silver-cloride.

Figure 2:
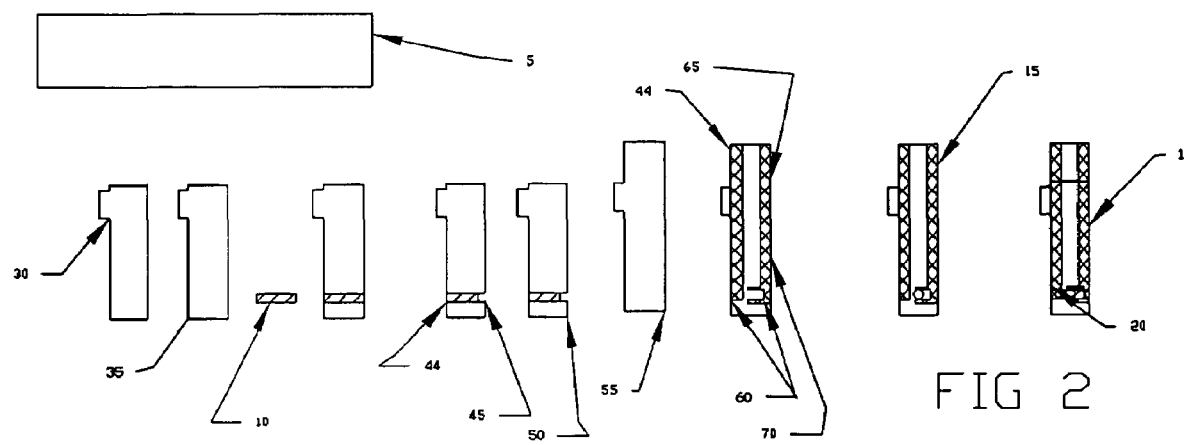
FIG. 2 is a front of an alternate strip-supported electrode configuration.

FIG. 2 shows the strip (1) is formed by applying a small section of uniformly coated CNT and binder material (10). Then traditional conductive ink leads (15) are sandwiched together with the uniformly coated CNT and binder material piece to form the completed electrodes (20). The material formed from single-walled or multi walled nanotubes and may be formed from multiple layers or dispersions containing, carbon nanotubes, carbon nanotubes/antimony tin oxide, carbon nanotubes/platinum, or carbon nanotubes/silver or carbon nanotubes/silver-cloride. Alternatively the strip could be made by first screen printing the electrodes leads and then screen printing the CNT and binder material (10) so that it overlaps the distal ends of the electrodes (20) leads.

The process of forming the strip (1) in FIG. 2 is as follows:
a) A piece of thin plastic film is coated with CNT and polymer binder forming (5).
b) The coated thin plastic film (55) is cut into a small well defined strip forming (10).
c) A plastic film is cut to form a handle (30).
d) Adhesive (35) is applied to the handle (30) forming handle (40).
e) The small section of coated thin plastic film (10) is applied to the handle (40) defining the active electrode (44) of the strip.
f) A small notch (45) is punched into the coated thin plastic film (10) applied to the handle (30) further defining the active electrode (44) of the strip (1) which is new sub part (50).
g) A plastic film (55) is cut to form a mirror image of the first handle (30).
h) Conductive carbon ink (60) is applied to the second handle (55) using conventional screen printing means and dried to conductive lead for active electrode (44), working electrode (65) and the reference electrode (66). This forms new sub part (70).
i) The AG/CL electrode is formed by spraying the colloidal AG/CL to a specific electrode while positioning a mask to hide the areas where the AG/CL is not desired.
j) A glucose oxidase based reagent mixture is applied to the active electrode (44).

k) The first sub part (50) and second sub part (70) are positioned and the conductive traces are brought into contact to form a complete electrode system (80) of the strip.

Another embodiment of the invention uses test strips made from the aforementioned forming means. However, the final step of the manufacturing process prior to applying the glucose oxidase reagent mixture, which is formulated without the associated mediator, is to apply a mixture of platinum to one or more of the electrodes. The platinum is a concentration of 40% by weight in aqueous type solution of platinum nanoparticles similar to that sold by Pred Materials International, Inc., 60 East 42nd Street, Suite 1456, New York, N.Y. 10165 is used. The platinum solution can be applied by ink jetting which can be accomplished by using precision components from the Lee Company of Westbrook, Conn., such as the VHS-S/P 10+ Nanoliter Dispensing Valves. Additionally, the platinum can be added to the carbon nanotube ink by introducing the desired amount of nano size particles (similar in size to the carbon) into the carbon nanotube ink. The nano size platinum material can be obtained from Sigma-Aldrich company item 483966, platinum nanosize activated powder, which can be added to the dispersion to achieve a percent weight of between 0.5% and 10%. The glucose oxidase reagent mixture, which is formulated without the associated mediator, is then applied to the working electrode (44).

The next preferred method of the invention to form a strip is mechanical formation of the electrodes in FIG. 1. The electrodes are formed mechanically after coating the conductive ink (199) on a flexible film (200). The ink can be formed from single-walled or multi walled nanotubes and may be formed from multiple layers or dispersions containing, carbon nanotubes, carbon nanotubes/antimony tin oxide, carbon nanotubes/platinum, or carbon nanotubes/silver or carbon nanotubes/silver-cloride. This forms conductive material (201) when cured properly. The strip (1) electrodes are formed from CNT material (201) by mechanically removing the CNT material (201) to form the active electrode (244), working electrode (265) and the reference electrode (266). The CNT material (201) can be removed by various means as shown in FIG. 5 through FIG. 10. After forming the electrodes the AG/CL electrode is formed by spraying the colloidal AG/CL to a specific electrode while positioning a mask to hide the areas where the AG/CL is not desired.

Figure 4:
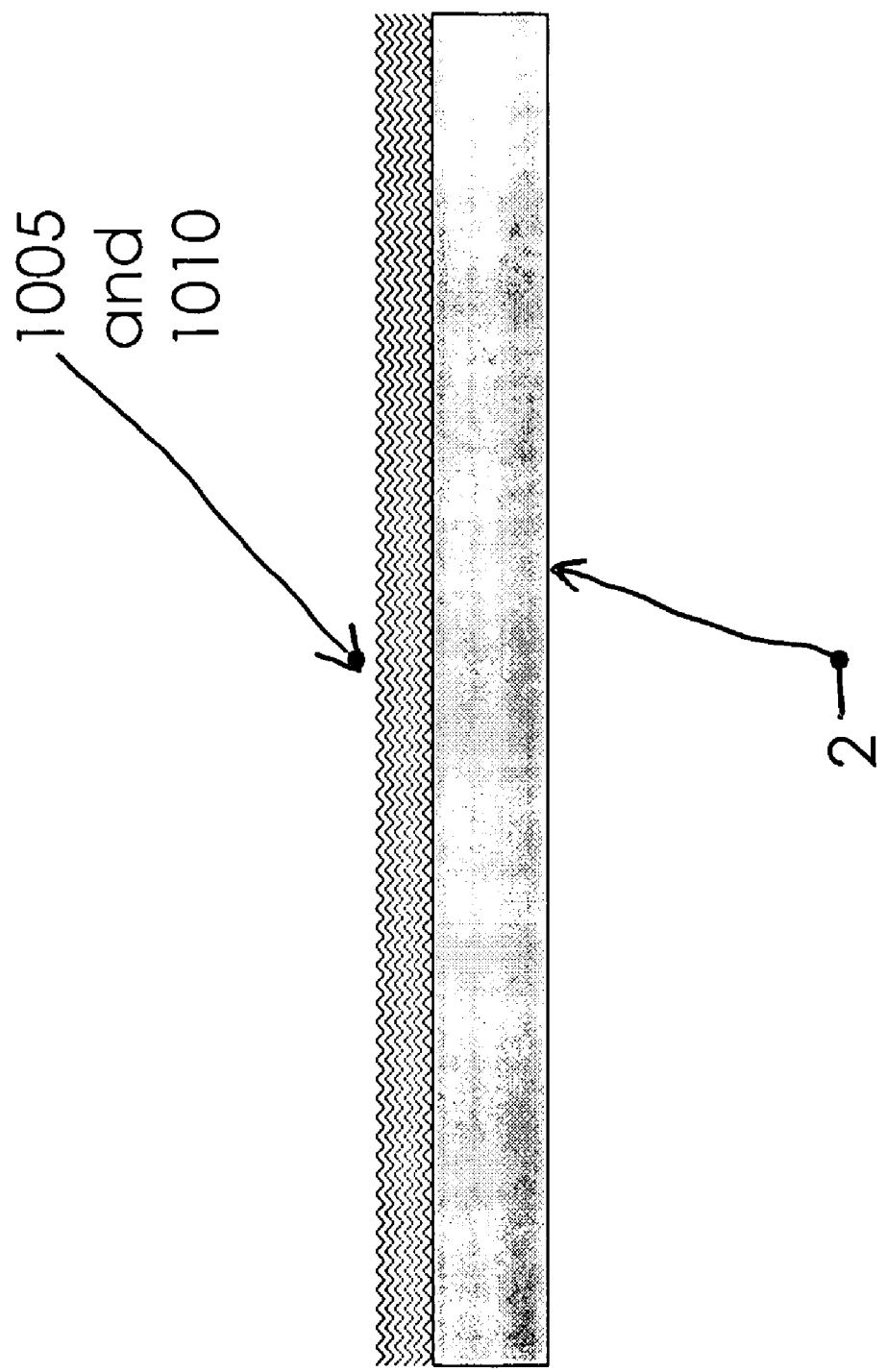
FIG. 4 shows CNT inks or dispersion coated on Polyester.

FIG. 4 shows conductive material of the invention coated (1005 and 1010) on Polyester (2).

Figure 5:
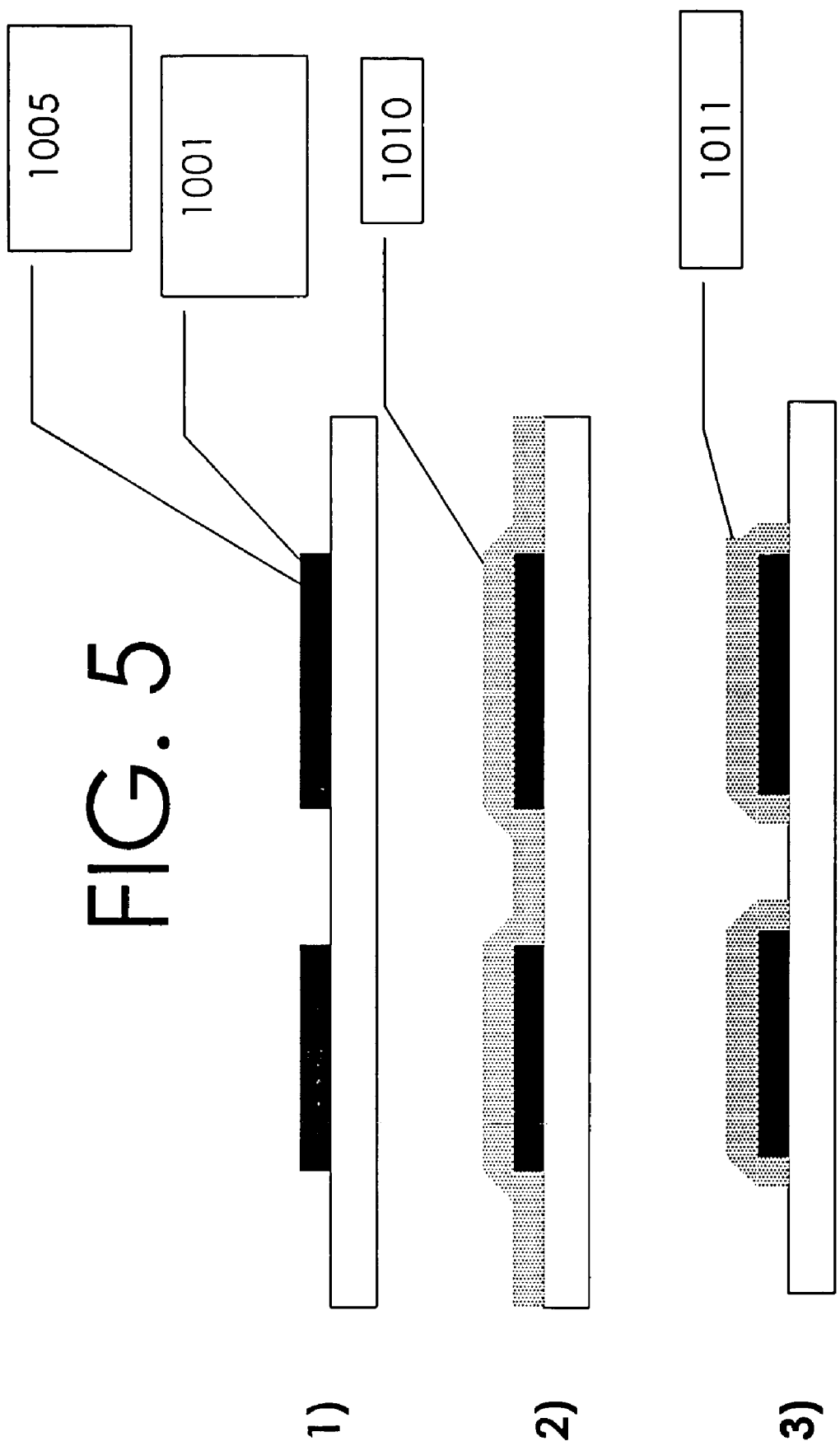
FIG. 5 is a two part CNT ink or dispersion formed by inkjet printing.

FIG. 5 is two part CNT ink with inkjet printing means of forming the electrodes in FIG. 1. The ink jet prints the image (1001) of the electrode to be formed with the Carbon Nanotube material (CNT) (1005) bearing ink. The non conductive polymer binder is applied over the entire area coating both the inkjet printing and non printed areas. The polymer binder (1010) can then be removed leaving behind CNT formed electrodes. The polymer binder (1010) can be removed by either chemical or mechanical means such as a Universal Laser Systems of Phoenix Ariz., VersaLaser product to form (1011). Alternatively the polymer binder (1010) can also be left on the entire surface because the conductive CNT material (1005) is the electrode and the polymer binder is non conductive. The polymer binder (1010) is porous and is selected to provide wear resistance and is not in itself conductive. A polyurethane base binder is used to cover the carbon nanotubes. The area coated with the CNT ink (1005) is conductive and forms the electrodes.

Figure 6:
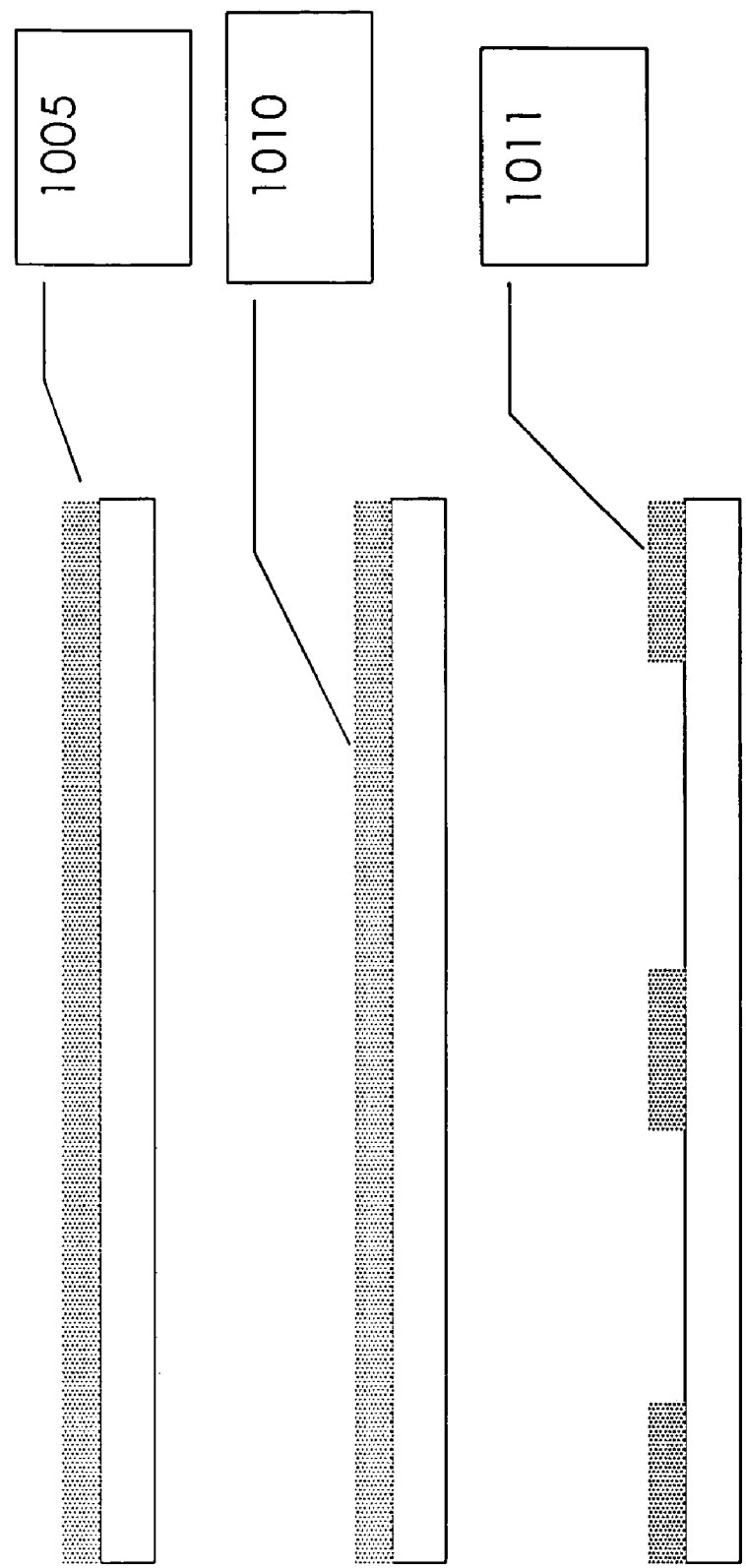
FIG. 6 shows a screen printed polymer binder method.

FIG. 6 shows a screen printed polymer binder method of application means for forming the electrodes in FIG. 1. In this embodiment the ink (1005) is applied uniformly over the entire surface of the strip. The polymer binder (1010) is then screen printed onto the strip (1) defining the electrodes. The ink (1005) is then removed from the unprotected areas mechanically or by use of a laser such as a Universal Laser Systems of Phoenix Ariz., VersaLaser product to form (1011).

Figure 7:
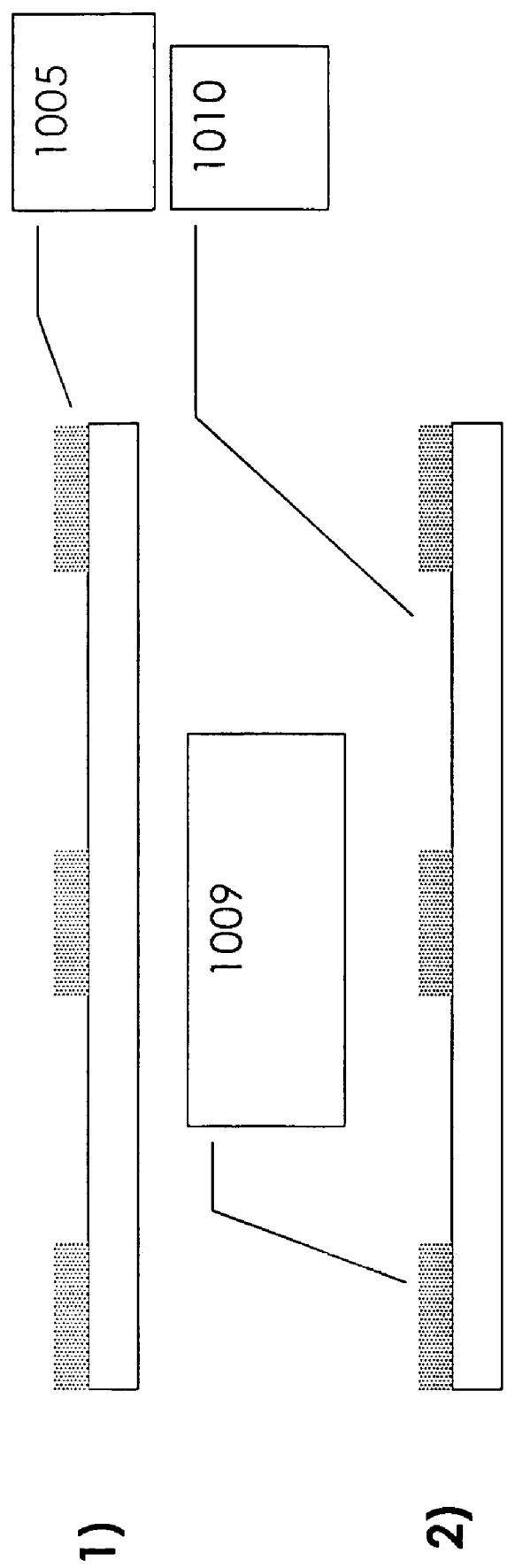
FIG. 7 shows a CNT printed coating method.

FIG. 7 shows a printed coating method for forming the electrodes in FIG. 1. For a one part ink the CNT ink (1005) is printed on the flexible substrate to define the electrodes. The polymer binder (1010) is then applied to the whole surface of the strip, and the CNT coated areas define the electrodes (1009). The printing can be accomplished by screen printing, ink jet printing, gravure, flexo, pad printing or other printing means.

Figure 8:
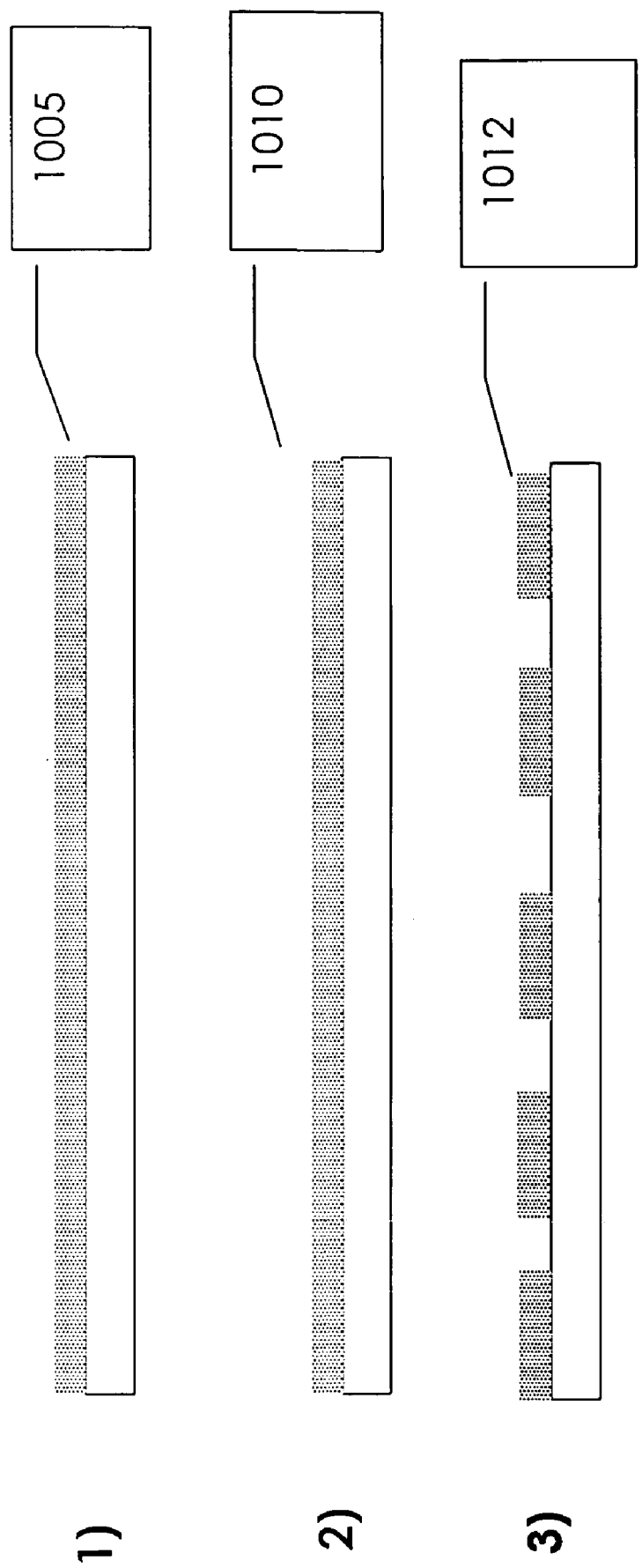
FIG. 8 shows a laser removal method.

FIG. 8 shows a laser removal method for forming the electrodes in FIG. 1. The CNT ink (1005) is applied either as a two part coating or a one part coating with the polymer binder (1010). A laser such as the Universal laser Systems Versalaser is used to remove the CNT (1005) and polymer binder (1010) to form the conductive areas of the strip (1012).

Figure 9:
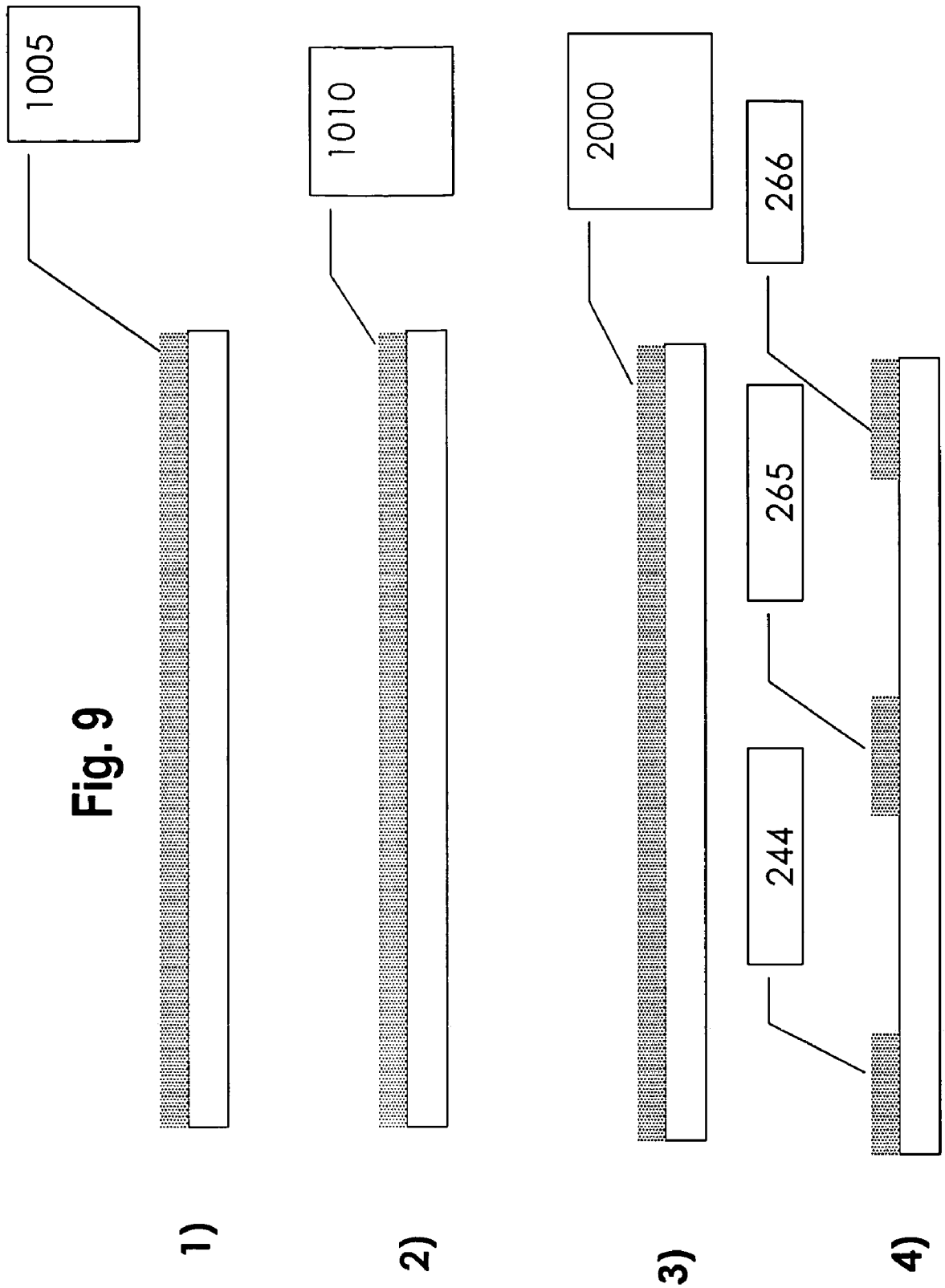
FIG. 9 is the photolithography method.

FIG. 9 is the photolithography method using a CNT ink (1005) for forming the electrodes in FIG. 14. The CNT ink (1005) and polymer binder (1010) coating is applied then a photolithography definable mask (2000) is applied. The strip (1) is exposed, developed and the undeveloped areas are removed using an etching process. The photolithography definable mask is then removed to expose the formed electrodes (244), (265, 266).

Figure 10:
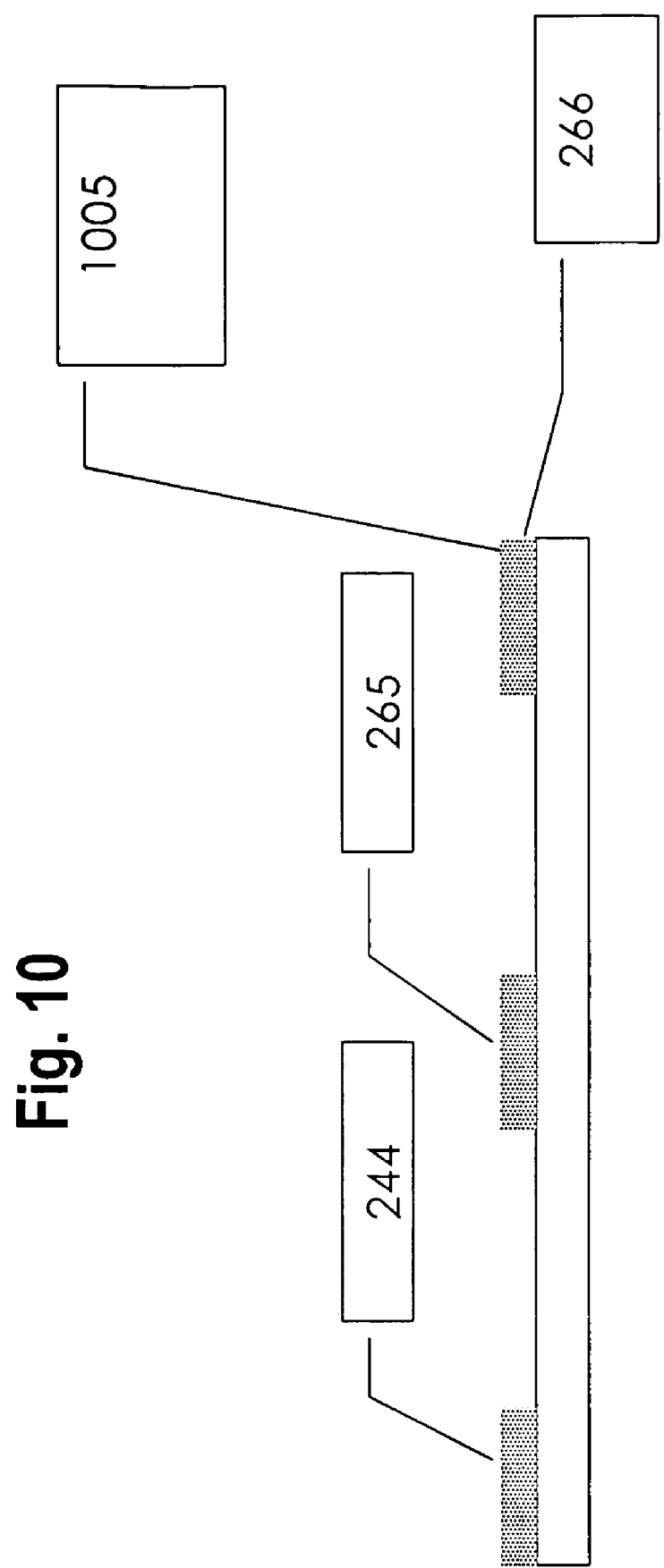
FIG. 10 is a one part ink printed by conventional processes.

FIG. 10 is a one part ink (1005) printed electrodes formed by conventional processes such as screen printing, ink jet printing, gravure, flexo, pad printing or other printing means. The one part ink (1005) can be formed from single-walled or multi walled nanotubes and may be formed from multiple layers or dispersions containing, carbon nanotubes, carbon nanotubes/antimony tin oxide, carbon nanotubes/platinum, or carbon nanotubes/silver or carbon nanotubes/silver-cloride. The formed electrodes (244), (265, (266) are printed images resulting from the printing process.

Figure 3:
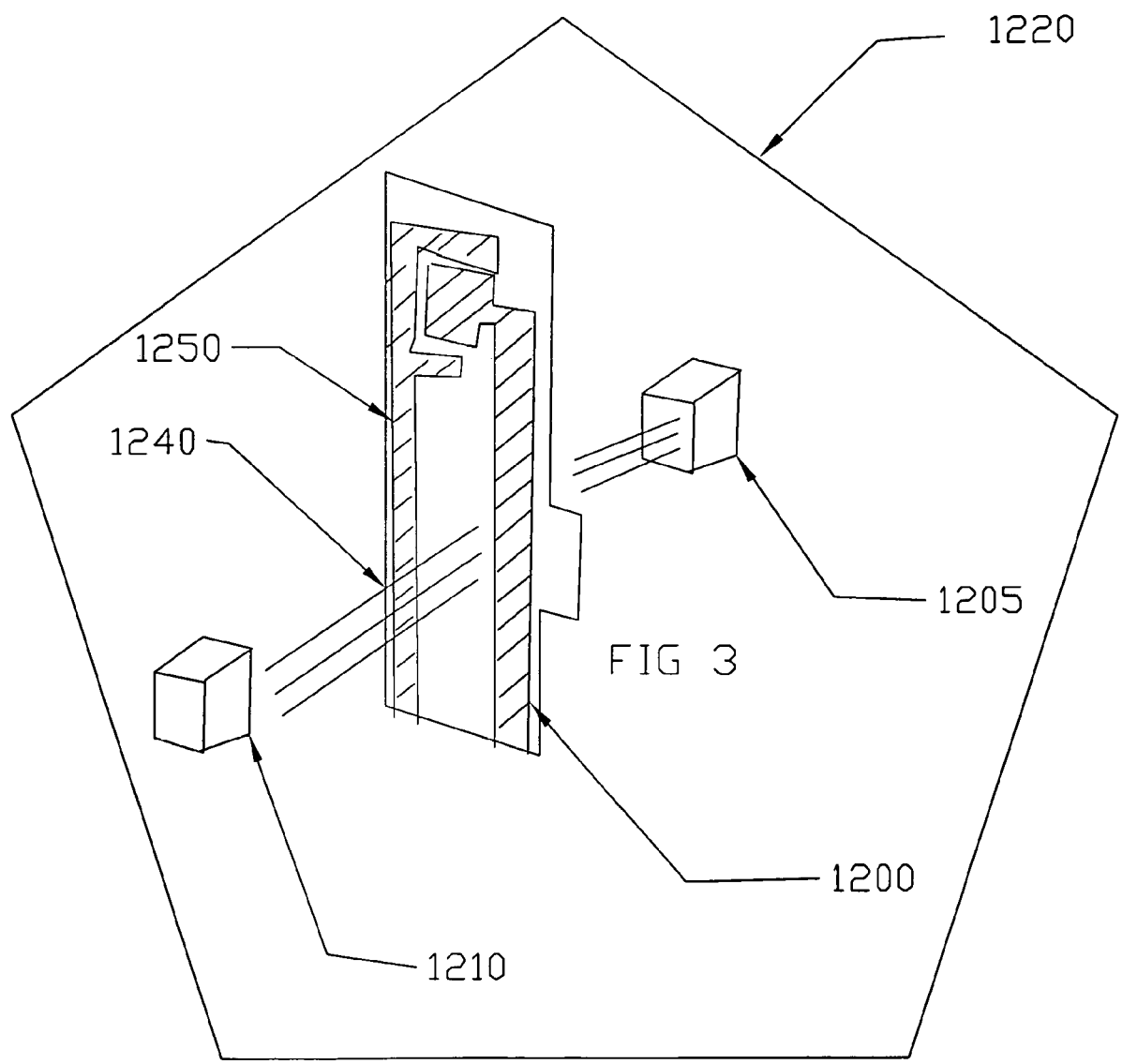
FIG. 3 is a schematic of using a transparent conductor coating as a means of preventing off brand test strip use.

The FIG. 3 is a schematic of using a transparent conductor coating as a means of preventing off brand test strip use. The use of the transparent conductive carbon nanotube coatings (1200) also permits the manufacturer from having alternative brand test strips used in their meters. The use of the transparent conductor prevents inferior or poorly manufactured product to be detected and prevented from being used in the test device designed for use with a strip of the invention. The transparent nature of the conductor when used with an appropriately configured LED (1205) and photo detector system (1210) can prevent the utilization of non branded product being used in the test device. The test strip (1215) is inserted in test meter (1220) not shown. The LED (1205 and photo detector (1210) are positioned within test meter (1220) such that when the test strip (1200) is in meter (1220) the test strip (1200) is positioned between LED (1205) and photo detector (1210) so that at least one of the electrode leads (1250) is in a direct path of LED light (1240). The electronics (1230) not shown in test meter (1220) only enables the sensing circuits (1240) not shown in test meter (1220) to test the strip (1) if the LED (1205) light (1240) and photo detector (1210) can receive light (1240). This requires that the electrode leads (1250) are transparent and able to transmit the LED light (1240).

Use of the Electrochemical Test Device

To illustrate the use of an electrochemical test device of this invention, the following glucose assay is described. It will be understood, however, that by selecting the proper reagent, other analytes may be determined using these procedures.

Reagents

Various types of analytical or electrochemical sensor reagents may be applied to the electrodes. To create a functional electrochemical test device, a reagent chemistry must be selected based on the analyte to be tested and the desired detection limits. Preferably, the reagent is deposited on the specific electrodes such that a uniform amount is applied from sensor to sensor and the reagent is applied uniformly over the appropriate electrodes. The reagent may be applied using any conventional procedure, such as screen printing, inkjet printing, or discrete application using IVEK pumps or any other drop on demand system capable of delivering consistent and uniform volume of reagent.

The specific electrodes coated will depend on the specific reagent(s) employed. Typically, the reagent is applied to the working electrode, but may in some cases also be applied to the other electrodes. After the reagent has been placed on the appropriate electrodes, it is typically dried. Subsequently, when the test device is used, the test sample of aqueous fluid, such as blood, rehydrates the reagent and a potential [is applied to the electrodes from which a current measurement may be taken by a meter.

An example reagent formulation suitable for use in the present invention is described below. This reagent may be used to determine the presence or concentration of glucose in an aqueous fluid sample. Preferably, this reagent formulation is used with an electrochemical sensor having a counter electrode, working electrode and reference electrode.

Reagent Formulation

| Material | Amount/Concentration |
| --- | --- |
| 2-(N-morpholino) ethanesulfonic acid | (MES 100 millimolar (mM) buffer) |
| Triton X-100 | 0.08% wt/wt |
| Polyvinyl alcohol (PVA) mol. wt. 10K 88% hydrolized | 1.00% wt/wt |
| Imidazole osmium mediator, reduced, as defined in U.S. Pat. No. 5,437,999 | 6.2 mM |
| Glucose Oxidase | 6000 units/mL |

The above patent disclosure is incorporated herein by reference in its entirety.

The above reagent formulation may be prepared using the following procedures:

(a) 1.952 grams of MES buffer is added to 85 mL of nanograde water. The mixture is stirred until the components dissolve. The pH of the solution is adjusted to 5.5 with NaOH. The volume of the solution is then brought to 100 mL of final buffer solution.

(b) 0.08 grams of Triton X-100 and 1 gram of PVA is added to a beaker capable of holding all the components (e.g., a 200 mL beaker). The buffer solution is added to bring the total solution weight to 100 grams. The mixture is heated to boiling and stirred to dissolve the PVA.

(c) 4.0 mg of the reduced osmium mediator is added to 1 mL of the solution from step (b) above. The mixture is stirred to dissolve the mediator.

(d) The mixture is left to cool to room temperature.

(e) 6000 units of glucose oxidase are added and the mixture is mixed until the enzyme is dissolved.

The above reagent formulation may be used to determine the presence or concentration of glucose in an aqueous fluid sample. As will be apparent to those skilled in the art, other reagent formulations may be employed to assay different analytes. Such reagent formulations are well known in the art. Typically, such reagent formulations are designed to react specifically with the desired analyte to form a measurable electrochemical signal.

Without being limited to theory, it is believed that in the example reagent formulation described above, glucose is anaerobically oxidized or reduced with the involvement of the enzyme and the redox mediator. Such a system is sometimes referred to as an amperometric biosensor. Amperometry refers to a current measurement at constant applied voltage on the working electrode. In such a system, the current flowing is limited by mass transport. Therefore, the current is proportional to the bulk glucose concentration. The analyte, enzyme and mediator participate in a reaction where the mediator is either reduced (receives at least one electron) or oxidized (donates at least one electron). The glucose reaction ends when glucose oxidase is oxidized and the mediator is reduced. The mediator is then oxidized at the surface of the working electrode by the applied potential difference. Changes in the system amperage result from changes in the ratio of oxidized/reduced forms of the redox mediator. The amperage change directly correlates to the detection or measurement of glucose in the test sample.

Various enzymes may be used in the reagent formulations employed in this invention. The particular enzyme employed will vary depending on the analyte to be detected or measured. Preferred enzymes include glucose oxidase, glucose dehydrogenase, cholesterol esterase and alcohol oxidase. The amount of enzyme employed will generally range from about 0.5 to about 3.0 million units of enzyme per liter of reagent formulation.

The electrodes of the electrochemical test device are prepared as described above and the electrode is coated with 1.0 µL (micro liter) of the above-described reagent formulation and dried.

The electrochemical test device is then inserted in a meter before the test sequence is initiated. Any suitable meter device which has contacts that interface with the test device contacts may be employed. Such metering devices are well known in the art. The meter will generally contain a measuring circuit and be adapted to apply an algorithm to the current measurement whereby the analyte level is provided and visually displayed. Examples of suitable power sources and meters may be found, for example, in U.S. Pat. Nos. 4,963,814; 4,999,632; and 4,999,582 to Parks et al., U.S. Pat. No. 5,243,516 to White et al., and European Patent Application No. 89116797.5, to Hill et al. The disclosures of these patents are incorporated by herein by reference in their entirety.

A small sample of body fluid or other aqueous fluid is then applied to the test device. The current is measured about 10 to about 30 seconds after applying the sample. The current is read by the meter between the working and counter electrode and, optionally, is compared to the reference electrode, if it is present. The meter then applies the algorithm to the current measurement and converts the measurement to an analyte concentration. This analyte level is visually displayed on the meter.

From the foregoing description, various modifications and changes in the electrochemical test devices, processes and methods of this invention will occur to those skilled in the art. All such modifications coming within the scope of the appended claims are intended to be included therein.

Alternatively in an alternate embodiment a clear or transparent electrode coating can be used to prevent off brand utilization of test strips by using an LED and detector to transmit and receive light through the conductor which cannot be done with existing conductive materials because they are not transparent. This is done by first selecting a clear handle material such as polyester and then using a suitable LED and detector circuit as part of the test meter and positioning it such that the LED transmits through the clear handle material and the electrode from the transparent carbon nanotube conductive material. If the corresponding LED does not detect the LED then the electrodes can not be made of the transparent carbon nanotube conductive material and the test is aborted by programming contained in the meter.

Additionally the strip (1) electrode can be coated both as one part or two part inks such that the electrodes are formed with well defined edges and smooth surface morphology to produce a consistent surface area with minimal surface area variation from strip to strip.

Additionally as shown in FIG. 4 CNT ink can be coated on Polyester handle which forms a transparent handle that is capable of permitting light to transmit through the test strip. When used with the appropriate light detection means FIG. 4 incorporated on the meter, the strip can prevent the use of un-licensed product in the meter Additionally as shown in FIG. 5 is two part CNT ink with inkjet printing means of forming the electrodes in FIG. 1. The ink jet prints the image (1001) of the electrode to be formed with the Carbon Nanotube material (CNT) (1005) bearing ink. The non conductive polymer binder is applied over the entire area coating both the inkjet printing and non printed areas. The polymer binder (1010) can then be removed leaving behind CNT formed electrodes. The polymer binder (1010) can be removed by either chemical or mechanical means such as a Universal Laser Systems of Phoenix Ariz., VersaLaser product to form (1011). Alternatively the polymer binder (1010) can also be left on the entire surface because the conductive CNT material (1005) is the electrode and the polymer binder is not conductive. The polymer binder (1010) is porous and is selected to provide wear resistance and is not in itself conductive. A polyurethane base binder is used to cover the carbon nanotubes. The area coated with the CNT ink (1005) is conductive and forms the electrodes.

Additionally FIG. 6 shows a screen printed polymer binder method of application means for forming the electrodes in FIG. 1. In this embodiment the ink (1005) is applied uniformly over the entire surface of the strip. The polymer binder (1010) is then screen printed onto the strip (1) defining the electrodes. The ink (1005) is then removed from the unprotected areas mechanically or by use of a laser such as a Universal Laser Systems of Phoenix Ariz., VersaLaser product to form (1011).

Additionally FIG. 7 shows a printed coating method for forming the electrodes in FIG. 1. The CNT ink (1005) is printed on the flexible substrate to define the electrodes. The polymer binder (1010) is then applied to the whole surface of the strip, and the CNT coated areas define the electrodes (1009). The printing can be accomplished by screen printing, ink jet printing, gravure, flexo, pad printing or other printing means.

Additionally FIG. 8 shows a laser removal method for forming the electrodes in FIG. 1. The CNT ink (1005) is applied either as a two part coating or a one part coating with the polymer binder (1010). The polymer binder (1010 used can also be conductive such as Acheson Electrodag 427 Antimony Tin Oxide (ATO) ink. A laser such as the Universal laser Systems Versalaser is used to remove the CNT (1005) and polymer binder (1010) to form the conductive areas of the strip (1012).

Additionally FIG. 9 shows the photolithography method using a one part CNT ink (1005) for forming the electrodes in FIG. 14. The CNT ink (1005) and polymer binder (1010) coating is applied, then a photolithography definable mask (2000) is applied. The strip (1) is exposed, developed and the undeveloped areas are removed using an etching process. The photolithography definable mask is then removed to expose the formed electrodes (244), (265, (266). The photolithography technique can be extended to a two part ink system if it is desired. To do so may require two photolithography steps for the conductive CNT ink and one for the polymer binder however one step has been found to be acceptable. The polymer binder (1010 used can also be conductive such as Acheson Electrodag 427 Antimony Tin Oxide (ATO) ink.

Conventional photolithography techniques or other electronic circuit fabrication technologies are used to form the electrodes. In the first step of a typical process, a photoresist material is applied to the conductive layer and dried. Any suitable photoresist material may be employed, including both negative and positive photoresist materials. A preferred material is the negative semi-aqueous resist available from Dupont under the tradename "Resiston".

A developer mask is then positioned over the photoresist layer. The mask can be either a contact or non-contact type. The patterning and masking methods that can be employed to form the electrode shapes, conductive lines, contact pads, etc., according to this invention can include mechanical masks, contact masks and the like, as well as other methods useful herein. For example, Chapter 14 of the above mentioned Harper, Handbook of Materials and Processes for Electronics, can be referred to for such methods. The developer mask, which has cutout portions in the shape of the electrodes, only covers a portion of the photoresist layer leaving a portion of photoresist layer exposed. The uncovered or exposed photoresist layer is then irradiated with ultraviolet (UV) light. Upon exposure to ultraviolet light, the photoresist material becomes insoluble in the developer solvent. The UV-exposed, insoluble photoresist material is termed "patterned photoresist". The developer mask is then removed and the photoresist layer is contacted with developer to remove the photoresist material previously covered by the developer mask. The developer used in this step will vary depending on the particular photoresist material employed. Typically, the proper developer for use with a particular photoresist will be specified by the manufacturer of the resist material. When "Resiston" is used as the photoresist, the developer/solvent recommended by Dupont should be employed and careful attention paid to recommended procedures. If an alternate photoresist is selected, such as Shipley "AZ-11", then an alternate developer would be used to remove the unexposed photoresist.

A chemical etchant is then used to remove the conductive layer no longer protected by the photoresist material. The chemical etchant does not remove the conductive material still protected by the remaining exposed, insoluble photoresist layer. Suitable chemical etchants include hydrofluoric acid or ammonium fluoride/hydrofluoric acid mixtures. A solvent is then applied to the patterned photoresist areas defining the electrodes to remove the patterned photoresist layer. Suitable solvents for removing the photoresist layer include, by way of example, sulfuric acid/dichromate or ammonia/hydrogen peroxide. Treatment with the solvent exposes the surface of the electrodes. Each electrode comprises three areas: a contact pad, a lead and an electrode area. Preferably, after exposure of the electrodes, the leads of each electrode are insulated by applying an epoxy resin material to the leads.

Optionally, the third electrode, if present, is then converted into a reference electrode by applying a suitable reference material. Suitable reference materials include silver/silver chloride, a mercury/mercury chloride and platinum/hydrogen materials. Such materials can be applied to the third electrode area of the reference electrode by any deposition method.

The electrochemical test device is then completed by applying an appropriate reagent to the working electrode. Suitable reagents for determining the presence or concentration of various analytes are well known in the art and are described in further detail herein below.

Additionally FIG. 10 shows a one part ink printed by conventional processes such as screen printing, ink jet printing, gravure, flexo, pad printing or other printing means. The one part ink (1005) can be formed from single-walled or multi walled nanotubes and may be formed from multiple layers or dispersions containing, carbon nanotubes, carbon nanotubes/antimony tin oxide, carbon nanotubes/platinum, or carbon nanotubes/silver or carbon nanotubes/silver-chloride. The formed electrodes (244), (265), (266) are the result of the printing method.

Additionally as shown in FIG. 3 is a schematic of using a transparent conductor coating as a means of preventing off brand test strip use. The use of the transparent conductive carbon nanotube coatings (1200) also permits the manufacturer from having alternative brand test strips used in their meters. This prevents inferior or poorly manufactured product to be detected and prevented from being used in the test device designed for use with a strip of the invention. The transparent nature of the conductor when used with an appropriately configured LED (1205) and photo detector system (1210) can prevent the utilization of non-branded product being used in the test device. The test strip (1215) is inserted in test meter (1220) not shown. The LED (1205) and photo detector (1210) are positioned within test meter (1220) such that when the test strip (1200) is in meter (1220) the test strip (1200) is positioned between LED (1205) and photo detector (1210) so that at least one of the electrode leads (1250) is in a direct path of LED light (1240). The electronics (1230) not shown in test meter (1220) only enables the sensing circuits (1240) not shown in test meter (1220) to test the strip (1) if the LED (1205) light (1240) and photo detector (1210) can receive light (1240). This requires that the electrode leads (1250) are transparent and able to transmit the led light (1240).

Additionally as shown in FIG. 2 the combination layer method can be used to form the electrodes in FIG. 1. The strip (1) is formed by applying a small section of uniformly coated CNT and binder material (10). Then traditional conductive ink leads (15) are sandwiched together with the uniformly coated CNT and binder material piece to form the completed electrodes (20). The process of forming the strip (1) is as follows:

a) A piece of thin plastic film is coated with CNT and polymer binder forming (5).
b) The coated thin plastic film (55) is cut into a small well defined strip forming (10).
c) A plastic film is cut to form a handle (30).
d) Adhesive (35) is applied to the handle (30) forming handle (40).
e) The small section of coated thin plastic film (10) is applied to the handle (40) defining the active electrode (44) of the strip.
f) A small notch (45) is punched into the coated thin plastic film (10) applied to the handle (30) further defining the active electrode (44) of the strip (1) which is new sub part (50).
g) A plastic film (55) is cut to form a mirror image of the first handle (30).
h) Conductive carbon ink (60) is applied to the second handle (55) using conventional screen printing means and dried to conductive lead for active electrode (44), working electrode (65) and the reference electrode (66). This forms new sub part (70).
i) The AG/CL electrode is formed by spraying the colloidal AG/CL to a specific electrode while positioning a mask to hide the areas where the AG/CL is not desired.
j) The first sub part (50) and second sub part (70) are positioned and the conductive traces are brought into contact form a complete electrode system (80) of the strip.
k) A glucose oxidase reagent mixture is applied to the active electrode (44).

Another embodiment of the invention uses test strips made from the aforementioned forming means. However, the final step of the manufacturing process prior to applying the glucose oxidase reagent mixture, which is formulated without the associated mediator, is to apply a mixture of platinum to one or more of the electrodes. The mixture of the platinum used is a concentration of 40% by weight in aqueous type solution of platinum nanoparticles similar to that sold by Pred Materials International, Inc., 60 East 42nd Street, Suite 1456, New York, N.Y. 10165. Additionally, the platinum can be added to the carbon nanotube ink by introducing the desired amount of nano size particles (similar in size to the carbon) into the carbon nanotube ink. The nano size platinum material can be obtained from Sigma-Aldrich company item 483966, Platinum Nanosize activated powder. The glucose oxidase reagent mixture which is formulated without the associated mediator is then applied to the working electrode (44).

The next preferred method of the invention to form a strip is mechanical formation of the electrodes in FIG. 1. The electrodes are formed mechanically after coating the CNT ink (199) on a flexible film (200). The ink can be formed from single-walled or multi walled nanotubes and may be formed from multiple layers or dispersions containing, carbon nanotubes, carbon nanotubes/antimony tin oxide, carbon nanotubes/platinum, or carbon nanotubes/silver or carbon nanotubes/silver-chloride. This forms CNT material (201) when cured properly. The strip (1) electrodes (244), (265), (266) are formed from CNT material (201) by mechanically removing the CNT material (201) to form the active electrode (244), working electrode (265) and the reference electrode (266). The CNT material (201) can be removed by various means as shown in FIG. 5 through FIG. 10. After forming the electrodes the AG/CL electrode is formed by spraying the colloidal AG/CL to a specific electrode while positioning a mask to hide the areas where the AG/CL is not desired.

Another embodiment uses a transparent conductor coating as a means of preventing off brand test strip use. The use of the transparent conductive carbon nanotube coatings (1200) also permits the manufacturer from having alternative brand test strips used in their meters. This prevents inferior or poorly manufactured product to be detected and prevented from being used in the test device design for use with a test strip of the invention. The transparent nature of the conductor when used with an appropriately configured LED (1205) and photo detector system (1210) can prevent the utilization of non branded product being used in the test device. The test strip (1215) is inserted in test meter (1220) not shown. The LED (1205) and photo detector (1210) are positioned within test meter (1220) such that when the test strip (1200) is in meter (1220) the test strip (1200) is positioned between LED (1205) and photo detector (1210) so that at least one of the electrode leads (1250) is in a direct path of LED light (1240) The electronics (1230) not shown in test meter (1220) only enables the sensing circuits (1240) not shown in test meter (1220) to test the strip (1) if the LED (1205) light (1240) and photo detector (1210) can receive light (1240). This requires that the electrode leads (1250) are transparent and able to transmit the LED light (1240).

Another embodiment of the invention uses test strips made from the aforementioned forming means. However, the final step of the manufacturing process prior to applying the glucose oxidase is to apply a mixture of platinum and water to one or more of the electrodes. The platinum can be applied by ink jetting which can be accomplished by using precision components from the Lee Company of Westbrook, Conn., such as the VHS-S/P 10+ Nanoliter Dispensing Valves A concentration of 40% by weight in aqueous type solution of platinum nanoparticles similar to that sold by Pred Materials International, Inc., 60 East 42nd Street, Suite 1456, New York, N.Y. 10165 is used.

Alternatively, the platinum can be added to the dispersion. A typical platinum can be acquired from Sigma-Aldrich company item 483966, Platinum Nanosize activated powder. To achieve the necessary platinum loading of the dispersion the platinum is added to the dispersion from approximately 0.5 to 10% of the weight of the dispersion and mixed thoroughly.

Other methods of applying or incorporating the platinum into the strip are envisioned such as incorporating it into the polymer binder as well as into the Carbon nanotube ink.

Although only a few exemplary embodiments of the present invention have been described in detail in this disclosure, those skilled in the art who review this disclosure will readily appreciate that many modifications are possible in the exemplary embodiments (such as variations in sizes, structures, shapes and proportions of the various elements, values of parameters, or use of materials) without materially departing from the novel teachings and advantages of the invention. Accordingly, all such modifications are intended to be included within the scope of the invention as defined in the appended claims.

Other substitutions, modifications, changes and omissions may be made in the design, operating conditions and arrangement of the preferred embodiments without departing from the spirit of the invention as expressed in the appended claims.

Additional advantages, features and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

All references cited herein, including all U.S. and foreign patents and patent applications, all priority documents, all publications, and all citations to government and other information sources, are specifically and entirely hereby incorporated herein by reference. It is intended that the specification and examples be considered exemplary only, with the true scope and spirit of the invention indicated by the following claims. As used herein and in the following claims, articles such as "the", "a" and "an" can connote the singular or plural.

What is claimed is:

1. An electrochemical test device for determining the presence or concentration of an analyte in an aqueous fluid sample, said electrochemical test device comprising:
   (a) a substrate, the substrate comprising a non-conductive material;
   (b) a working electrode comprising a conductive film formed with carbon nanotubes and other conductive and non conductive materials affixed to the non-conductive substrate, said working electrode having a first electrode area, a first lead and a first contact pad;
   (c) a counter electrode comprising a conductive film formed with carbon nanotubes and other conductive and non conductive materials affixed to the non-conductive substrate, said counter electrode having a second electrode area, a second lead and a second contact pad;
   (d) a reagent capable of reacting with the analyte to produce a measurable change in potential which can be correlated to the presence or concentration of the analyte in the fluid sample, said reagent overlaying at least a portion of the first electrode area of the working electrode; and
   (e) a reference electrode comprising a conductive coating formed with carbon nanotubes and other conductive and non conductive materials affixed to the non-conductive substrate, said reference electrode having a third electrode area, a third lead, and a third contact pad, and wherein at least a portion of the third electrode area is overlaid with a reference material.

2. The device of claim 1, wherein said reference material is silver/silver chloride.

3. The device of claim 1, wherein the substrate comprises a flexible material.

4. The device of claim 1, wherein the conductive film is formed from single and multi walled carbon nanotubes and the average outer diameter size of the carbon nanotubes is greater than 0.5 nm.

5. The device of claim 1, wherein said nanotubes are selected from the group consisting of single-walled nanotubes (SWNTs), double-walled nanotubes (DWNTs), multi-walled nanotubes (MWNTs), and mixtures thereof.

6. The device of claim 1, wherein said nanotubes are substantially single-walled nanotubes (SWNTs).

7. The device of claim 1, wherein said nanotubes are present in said film at about 0.001 to about 10% based on weight.

8. The device of claim 1, wherein said nanotubes are present in said film at about 0.5%.

9. The device of claim 1, wherein the film has a surface resistance in the range of less than about 50,000 ohms/square.

10. The device of claim 1, further comprising a polymeric material.

11. The device of claim 1, wherein said nanotubes are selected from the group consisting of single-walled nanotubes (SWNTs), double-walled nanotubes (DWNTs), multi-walled nanotubes (MWNTs), and mixtures thereof to form a dispersion.

12. A device of claim 11, wherein the dispersion comprises a plurality of nanotubes with an outer diameter of less than 10 nm.

13. The device of claim 12, wherein said nanotubes have an outer diameter of about 0.5 to 10 nm.

14. The device of claim 12, wherein said nanotubes are substantially single-walled nanotubes (SWNTs).

15. The device of claim 11, wherein the dispersion further comprising a polymeric material, wherein the polymeric material comprises a material selected from the group consisting of thermoplastics, thermosetting polymers, elastomers, conducting polymers and combinations thereof.

16. The device of claim 11, the dispersion further comprising a polymeric material, wherein the polymeric material comprises a material selected from the group consisting of ceramic hybrid polymers, and phosphine oxides chalcogenides.

17. The device of claim 11, the dispersion further comprising a plasticizer, softening agent, filler, reinforcing agent, processing aid, stabilizer, antioxidant, dispersing agent, binder, a cross-linking agent, a coloring agent, a UV absorbent agent, or a charge adjusting agent.

18. The device of claim 11, the dispersion further comprising conductive organic materials, inorganic materials, or combinations or mixtures thereof.

19. The device of claim 18, wherein the conductive organic materials are selected from the group consisting of buckeyballs, carbon black, fullerenes, nanotubes with an outer diameter of greater than about 0.5 nm, and combinations and mixtures thereof.

20. The device of claim 19, wherein the conductive inorganic materials are selected from the group consisting of antimony tin oxide, iridium tin oxide, aluminum, antimony, beryllium, cadmium, chromium, cobalt, copper, doped metal oxides, iron, gold, lead, manganese, magnesium, mercury, metal oxides, nickel, platinum, silver, steel, titanium, zinc, and combinations and mixtures thereof.

21. The device of claim 20, further comprising a conductive material selected from the group consisting of tin-indium mixed oxide, antimony-tin mixed oxide, fluorine-doped tin oxide, aluminum-doped zinc oxide and combinations and mixtures thereof.

22. The device of claim 20, further comprising conductors, fluids, gelatins, ionic compounds, semiconductors, solids, surfactants, or combinations or mixtures thereof.

23. The device of claim 1, wherein the conductive coating is formed from single and multi walled carbon nanotubes and the average outer diameter size of the carbon nanotubes is less than 10 nm.

24. The device of claim 23, wherein said nanotubes are present in said coating at about 0.001 to about 10% based on weight.

25. The device of claim 23, wherein said nanotubes are present in said coating at about 0.05%.

26. The device of claim 1, wherein said film has a total light transmittance of about 90% or more.

27. The device of claim 1, wherein said film has a total light transmittance of about 95% or more.

28. The device of claim 1, wherein said film has a haze value less than 2.0%.

29. The device of claim 1, wherein said film has a haze value less than 0.1%.

30. The device of claim 1, wherein said film has a thickness between about 0.5 nm to about 1000 microns.

31. The device of claim 1, wherein the nanotubes are oriented.

32. The device of claim 1, wherein the nanotubes are oriented in the plane of the film.

33. The device of claim 1, wherein the nanotubes are oriented, further comprising an additional layer of oriented nanotubes.

34. The device of claim 1, wherein the conductive film of at least one of the working electrode and the counter electrode contains platinum.

35. The device of claim 1, wherein the substrate comprises a polymeric sheet.

36. The device of claim 35, wherein the polymeric sheet material is selected from the group consisting of polyesters, polycarbonates and polyimides.

37. The device of claim 1, wherein the conductive coating is formed with carbon nanotubes and other conductive materials.

38. The device of claim 1, wherein the reagent comprises an enzyme and a redox mediator.

39. The device of claim 38, wherein the enzyme is glucose oxidase.

40. The device of claim 38, wherein the redox mediator is potassium ferricyanide.

41. The device of claim 1, wherein the conductive coating formed with carbon nano tubes and other conductive and non conductive materials has a surface texture less than 0.33 microns.

42. The device of claim 1, wherein the conductive coating formed with carbon nano tubes and other conductive materials has a surface texture less than 0.33 microns.

43. An electrochemical test device for determining the presence or concentration of an analyte in an aqueous fluid sample, said electrochemical test device comprising:
 (a) a substrate, the substrate comprising a non-conductive material;
 (b) a working electrode comprising a conductive film formed with carbon nanotubes and other conductive and non conductive materials affixed to the non-conductive substrate, said working electrode having a first electrode area, a first lead and a first contact pad;
 (c) a counter electrode comprising a conductive film formed with carbon nanotubes and other conductive and non conductive materials affixed to the non-conductive substrate, said counter electrode having a second electrode area, a second lead and a second contact pad;
 (d) a reagent capable of reacting with the analyte to produce a measurable change in potential which can be correlated to the presence or concentration of the analyte in the fluid sample, said reagent overlaying at least a portion of the first electrode area of the working electrode; and wherein at least one of the conductive films forms at least one electrode that has a platinum layer.

44. An electrochemical test device for determining the presence or concentration of an analyte in an aqueous fluid sample, said electrochemical test device comprising:
 (a) a substrate, the substrate comprising a non-conductive material;
 (b) a working electrode comprising a conductive film formed with carbon nanotubes and other conductive and non conductive materials affixed to the non-conductive substrate, said working electrode having a first electrode area, a first lead and a first contact pad;
 (c) a counter electrode comprising an conductive film formed with carbon nanotubes and other conductive and non conductive materials affixed to the non-conductive substrate, said counter electrode having a second electrode area, a second lead and a second contact pad;

(d) a reagent capable of reacting with the analyte to produce a measurable change in potential which can be correlated to the presence or concentration of the analyte in the fluid sample, said reagent overlaying at least a portion of the first electrode area of the working electrode; and wherein the conductive films are formed with carbon nanotubes and other conductive materials and the leads are formed from coarse solid conductive material.

* * * * *